(12) United States Patent
Gao et al.

(10) Patent No.: US 7,115,565 B2
(45) Date of Patent: Oct. 3, 2006

(54) CHEMOTHERAPEUTIC MICROEMULSION COMPOSITIONS OF PACLITAXEL WITH IMPROVED ORAL BIOAVAILABILITY

(75) Inventors: Ping Gao, Portage, MI (US); Walter Morozowich, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 27 days.

(21) Appl. No.: 10/047,902

(22) Filed: Jan. 14, 2002

(65) Prior Publication Data

US 2002/0156124 A1 Oct. 24, 2002

Related U.S. Application Data

(60) Provisional application No. 60/262,555, filed on Jan. 18, 2001, and provisional application No. 60/284,608, filed on Apr. 17, 2001.

(51) Int. Cl.
*A61K 38/00* (2006.01)
*A01N 25/00* (2006.01)
*A61F 13/00* (2006.01)

(52) U.S. Cl. .............. 514/9; 424/405; 424/422
(58) Field of Classification Search ............ 514/9, 514/449, 411; 424/405, 422
See application file for complete search history.

(56) References Cited

U.S. PATENT DOCUMENTS

| | | | |
|---|---|---|---|
| 4,250,997 A | 2/1981 | Bodenmann et al. | 206/528 |
| 4,498,421 A | 2/1985 | Lovitt | 119/17 |
| 5,264,223 A | 11/1993 | Yamamoto et al. | 424/451 |
| 5,415,869 A | 5/1995 | Straubinger et al. | 424/450 |
| 5,424,073 A | 6/1995 | Rahman et al. | 424/450 |
| 5,439,686 A | 8/1995 | Desai et al. | 424/451 |
| 5,504,102 A | 4/1996 | Agharkar et al. | 514/449 |
| 5,641,803 A | 6/1997 | Carretta et al. | 514/449 |
| 5,648,090 A | 7/1997 | Rahman et al. | 424/450 |
| 5,665,382 A | 9/1997 | Grinstaff et al. | 424/450 |
| 5,670,537 A | 9/1997 | Canetta et al. | 514/449 |
| 5,683,175 A | 11/1997 | Golz | 362/338 |
| 5,728,687 A | 3/1998 | Bissery | 514/90 |
| 5,756,123 A | 5/1998 | Yamamoto et al. | 424/451 |
| 5,908,835 A | 6/1999 | Bissery | 514/33 |
| 5,916,596 A | 6/1999 | Desai et al. | 424/489 |
| 5,968,972 A | 10/1999 | Border et al. | 514/449 |
| 6,028,054 A | 2/2000 | Benet et al. | 514/9 |
| 6,057,359 A | 5/2000 | Eugster | 514/449 |
| 6,090,955 A | 7/2000 | Reszka et al. | 549/510 |
| 6,096,331 A | 8/2000 | Desai et al. | 424/422 |
| 6,136,846 A | 10/2000 | Rubinfeld et al. | 514/449 |
| 6,319,943 B1 | 11/2001 | Joshi et al. | 514/449 |
| 6,395,770 B1 * | 5/2002 | Broder et al. | 514/449 |
| 6,610,317 B1 * | 8/2003 | Straub et al. | 424/422 |
| 6,660,286 B1 * | 12/2003 | Lambert et al. | 424/405 |
| 2002/0025979 A1 * | 2/2002 | Kunz et al. | 514/411 |

FOREIGN PATENT DOCUMENTS

| | | |
|---|---|---|
| CH | 688 504 A5 | 10/1997 |
| EP | 0 211 079 | 2/1987 |
| EP | 0 919 228 | 6/1999 |
| EP | 1 029 539 | 8/2000 |
| GB | 2 257 359 | 1/1993 |
| WO | WO 96/05812 | 2/1996 |
| WO | WO 97/35527 | 10/1997 |
| WO | WO 98/53811 | 12/1998 |
| WO | WO 98/58927 | 12/1998 |
| WO | WO 99/06024 | 2/1999 |
| WO | WO 99/45918 | 9/1999 |
| WO | WO 00/18377 | 4/2000 |
| WO | WO 00/27367 | 5/2000 |
| WO | WO 00/28976 | 5/2000 |
| WO | WO 00/33862 | 6/2000 |
| WO | WO 00/72827 | 12/2000 |
| WO | WO 00/78247 | 12/2000 |
| WO | WO 01/03676 | 1/2001 |
| WO | WO 02/43765 | 6/2002 |

OTHER PUBLICATIONS

Ansel et al. (1995) *Pharmaceutical Dosage Forms and Drug Delivery Systems*, 6th Ed., pp 176–182.

Eiseman et al, *Plasma Pharmacokinetics and Tissue Distribution of Paclitaxel in $CD_2F_1$ Mice*, CANCER CHEMOTHER PHARMACO. 34:465–471 (1994).

Slater et al, *Comparsion of Cyclosporin A, Verapamil, PSC–833 and Cremophor EL As Enhancing Agents of VP–16 in Murine Lymphoid Leukemias*, LEUKEMIA RESEARCH 19(8):543–548 (1995).

International Search Report for International Patent Application No. PCT/US02/00497.

Sharma et al, *Novel Taxol® Formulation: Polyvinylpyrrolidone Nanoparticle–Encapsulated Taxol® for Drug Dellvery in Cancer Therapy*, ONCOLOGY RESEARCH 9(7/8):281–286 (1996).

* cited by examiner

*Primary Examiner*—Jon Weber
*Assistant Examiner*—Suzanne M. Mayer
(74) *Attorney, Agent, or Firm*—Harness, Dickey & Pierce, P.L.C.

(57) ABSTRACT

Pharmaceutical compositions suitable for oral administration comprising paclitaxel, a solvent, a surfactant, a substituted cellulosic polymer, and optionally but preferably a P-glycoprotein inhibitor. The composition may further comprise a diglyceride or mixture of diglyceride and monoglyceride. The composition generates a supersaturated paclitaxel microemulsion upon contact with water resulting in improved oral bioavailability of paclitaxel.

61 Claims, 2 Drawing Sheets

CHEMOTHERAPEUTIC MICROEMULSION COMPOSITIONS OF PACLITAXEL WITH IMPROVED ORAL BIOAVAILABILITY

CROSS-REFERENCE TO RELATED APPLICATIONS

This application claims the benefit of the following provisional applications: U.S. application Ser. No. 60/262,555 filed Jan. 18, 2001 and U.S. application Ser. No. 60/284,608 filed on Apr. 17, 2001, under 35 USC 119 (e)(i).

FIELD OF THE INVENTION

The present invention relates generally to formulations of chemotherapeutic agents and more specifically to formulations of paclitaxel and analogs thereof for oral administration.

BACKGROUND OF THE INVENTION

Paclitaxel is a clinically effective chemotherapeutic agent approved for the treatment of various cancers. However, because paclitaxel has very low water solubility (~10 μg/ml) which, due to a lack in suitable chemical functionality for salt formation, cannot be increased by pH adjustment, formulation of paclitaxel has proven difficult. As a result, most of the formulation work known in the art has been based on the use of co-solvents, surfactants and excipients (i.e., cyclodextrin) for intravenous (IV) formulations. Further, the oral bioavailability of paclitaxel has also been reported to be very low and as a result there is no oral formulation of paclitaxel on the market.

One of the commercially available intra-venous (IV) paclitaxel formulations is marketed under the trade name of Taxol® by Bristol-Myers/Squibb. Taxol® contains 6 mg/ml of paclitaxel, 527 mg/ml of a surfactant, (Cremophor EL, a polyethoxylated castor oil), and 49.7% (v/v) of absolute ethanol. This formulation requires a 5 to 20 fold dilution with either 5% dextrose or 0.9% NaCl solution which is then delivered by an intravenous infusion into the patient. Because of the low drug content in the Taxol formulation, a large volume of the formulation is administered to the patient in order to provide the required therapeutic doses (~135–170 mg/m$^2$). It is also worth noting that the amount of Cremophor EL necessary to deliver the required dose of paclitaxel in the Taxol formulation is considerably high (88 mg Cremophor EL per mg paclitaxel) and this vehicle has caused serious, life-threatening anaphylactoid reactions in animals and humans, even without paclitaxel. In addition, it has also been noted that that the Cremophor/ethanol formulation of paclitaxel precipitates upon dilution with infusion fluid and that fibrous precipitates are formed in some compositions when stored for extended periods of time. Additional information regarding disadvantages of paclitaxel compositions containing high concentrations of Cremophor may be found in U.S. Pat. No. 5,504,102 to Agharkar et al.

To alleviate the severe side-effects of the paclitaxel/cremophor formulations, patients are often required to receive premedication and/or prolonged paclitaxel infusion duration time of up to 24 hours. These measures, however, carry significant disadvantages. For example, the long infusion duration is inconvenient for patients, and is expensive due to the need to monitor the patients for the entire 6 to 24-hour infusion duration and the patient's prolonged stay in a hospital or treatment clinic. Similarly, premedication increases patient discomfort and increases the expense and duration of treatment. Moreover, such measures normally would not completely eliminate the side effects.

U.S. Pat. No. 5,641,803 to Canetta et. al. discloses a method of administering paclitaxel dosages of about 135 mg/m$^2$ via infusions of less than 6 hours duration. This method requires pretreatment of the patients with steroids, antihistamines, and H$_2$-receptor antagonists sufficient to prevent fatal anaphylactic-like reactions.

U.S. Pat. Nos. 6,136,846 and 6,319,943 disclose an oral formulation of paclitaxel which comprises paclitaxel, a solvent, and a pharmaceutically-acceptable, water-miscible solubilizer forming micelles, the solubilizer being selected from the group consisting of solubilizers having the general structures: R1 COOR2, R1 CONR2, and R1 COR2, wherein R1 is a hydrophobic C3–C50 alkane, alkene or alkyne and R2 is a hydrophilic moiety and wherein the solubilizer is selected such that it does not have a pKa less than about 6. The concentration of paclitaxel in the composition disclosed in U.S. Pat. Nos. 6,136,846 and 6,319,943 is 5–20 mg/g.

U.S. Pat. No. 5,648,090 to Rahman et. al. discloses a liposomal-encapsulated paclitaxel or an anti-neoplastic derivative thereof that is used to effect a therapeutically enhanced method of treating cancer, and may be used advantageously in combination with hyperthermia. The liposomes confer enhanced stability and solubility characteristics to paclitaxel or derivatives thereof.

U.S. Pat. No. 5,424,073 to Rahman et. al. discloses a liposomal-encapsulated paclitaxel or an anti-neoplastic derivative thereof which comprises a liposome forming material, cardiolipin, paclitaxel and a pharmaceutically acceptable carrier. The liposome forming material is phosphatidyl choline, cholesterol, and the like and the liposomes formed thereby may have a positive, negative or neutral charge. The liposomes confer enhanced stability and solubility to paclitaxel or derivatives thereof.

U.S. Pat. No. 6,090,955 to Reszka et. al. discloses a liposome-encapsulated paclitaxel composition that consists of a high paclitaxel concentration with high stability and hence a high therapeutic effect. The invention involves the development of specific forms of paclitaxel encapsulation and the use of these, optionally in combination with other substances, in the treatment of various types of tumor. The liposome consists of a lipid, an amphiphillic material, a polymer and a carrier liquid. The liposome-encapsulated paclitaxel is characterized in that it is prepared by high-pressure homogenization or by aerosol formulation.

U.S. Pat. No. 5,415,869 to Straubinger et. al. discloses a pharmaceutical composition for use in treatment of cancer patients comprised of at least one taxane and a mixture of one or more negatively charged phospholipids and one or more zwitterion (i.e. neutral) phospholipids. This mixture entraps the taxane in what is believed to be a liposome. The mixture contains a ratio of negatively charged phospholipids to zwitterion phospholipids of 1:9 to 7:3. The paclitaxel is present in an amount of 1.5–8.0 mole percent taxane. The composition is in the form of particles having a size of 0.025 to 10 microns with substantially no taxane crystals. One of the negatively charged phospholipids is diphosphatidyl choline, i.e. cardiolipin.

U.S. Pat. No. 5,683,715 to Boni et. al. discloses liposomal taxane formulations where the liposomal lipid is a phosphatidylcholine; these formulations are useful for treating animals afflicted with cancers.

U.S. Pat. No. 5,728,687 to Bissery discloses pharmaceutical compositions having therapeutic synergy comprising paclitaxel or taxotere or analogues thereof combined with at least one other therapeutically useful substance for treating neoplastic diseases. The other therapeutic substance is selected from the group consisting of an alkylating agent, epidophylloptoxin, an anti-metabolite or a vinca alkaloid.

U.S. Pat. No. 6,096,331 to Desai et. al. discloses and claims compositions and methods that are useful for the in-vivo delivery of taxane, wherein the taxane is formulated with a polymeric biocompatible material such as human serum albumin. The compositions are substantially cremophor-free and a variety of neoplastic tumors are treatable thereby.

U.S. Pat. No. 5,908,835 to Bissery discloses anti-tumor compositions comprising paclitaxel, taxotere or their derivatives in combination with an anthacycline antibiotic, the combination having a synergistic pharmacological activity greater than the expected additive effect of its individual components.

U.S. Pat. Nos. 5,665,382 and 4,498,421 to Grinstaff disclose and claim pharmaceutical compositions in which an active agent is encapsulated within a polymer shell whose cross-sectional dimension is no greater than 10μ. The shell consists of a biocompatible material such as proteins, lipids, polysaccharides and polynucleic acids all of which possess sulfhydryl groups that are cross-linked to form the shell. The pharmaceutical agent is any one of a number of generically disclosed groups excluding anti-cancer compounds.

U.S. Pat. Nos. 5,916,596 and 5,439,686 to Desai et. al. disclose pharmaceutical compositions comprising emulsions of polymer-encapsulated pharmaceutical agents including protein encapsulated paclitaxel. The polymer is a protein, polysaccharide, polypeptide or polynucleic acid cross-linked by disulfide bonds. The emulsion is any one of a wide variety of organic solvents.

Accordingly, there exists a clear need for oral compositions of paclitaxel that are easy to prepare, contain a high concentration of paclitaxel but a low surfactant level, cause fewer side effects, have improved stability and have high oral bioavailability.

SUMMARY OF THE INVENTION

An object of the present invention is to provide pharmaceutical compositions containing paclitaxel and analogs thereof which possess high oral bioavailability.

Another object of the present invention is to provide pharmaceutical compositions containing paclitaxel and analogs thereof which generate a supersaturated solution of the drug state in vivo whereby the oral bioavailability of paclitaxel is further enhanced.

A further object of the present invention is to provide a pharmaceutical composition containing a high drug load of paclitaxel for convenient administration.

Another object of the present invention is to provide pharmaceutical compositions which exhibit adequate physical and chemical stability as self-emulsifying formulations.

Still another object of the present invention is to provide pharmaceutical compositions containing paclitaxel which should cause fewer side effects in patients receiving the formulations.

Still another object of the present invention is to provide pharmaceutical formulations for paclitaxel which contain less polyethoxylated castor oil.

These and other objects of the present invention have been accomplished in the present invention. Accordingly, the present invention provides pharmaceutical compositions of paclitaxel in a form of self-emulsifying liquid composition comprising:

a) paclitaxel or an analog thereof, b) a pharmaceutically acceptable solvent, c) a pharmaceutically acceptable surfactant, and d) a substituted cellulosic polymer.

The compositions are self-emulsifying, capable of generating a supersaturated emulsion or a supersaturated microemulsion upon their exposure to an aqueous medium such as water or gastrointestinal fluid. The emulsion or a microemulsion permits rapid and efficient absorption of the paclitaxel resulting in enhanced bioavailibility of paclitaxel. The compositions of the present invention are primarily for oral administration. In a particular embodiment, the compositions further comprise a diglyceride or a mixture of diglyceride and monoglyceride. The amount of paclitaxel in the compositions can be up to about 100 mg/g. The high paclitaxel load in the compositions permits a reduced volume of the composition to be administered to the patients. The preferred solvents of the present invention include polyethylene glycol (PEG series), propylene glycol, ethanol, or a mixture thereof. The preferred surfactants include polyoxyl 40 hydrogenated castor oil (Cremophor RH40®), polyoxyl 35 castor oil (Cremophor EL®), polyoxyethylene sorbitan fatty acid esters (polysorbates), poloxamers (Pluronics), and vitamin E-TPGS 1000, with the more preferred surfactant being Cremophor EL®. The ratio of paclitaxel to the surfactant such as Cremophor in the composition of the present invention is generally less than 1:20, that means that for each part of paclitaxel less than twenty parts of the surfactant is required in the composition. The reduced amount of the surfactant in the composition as compared with that in the Taxol® formulation would significantly and desirably reduce the side effects caused by the Cremophor.

BRIEF DESCRIPTION OF THE DRAWINGS

In FIG. 2, the composition of Example 3 which contains HPMC shows rapid absorption with a high Cmax of about 300 ng/ml as compared to a low Cmax (around 13 ng/ml) with a formulation of similar composition without HPMC (Example 6). Approximately a 20-fold enhancement in the Cmax is observed from the composition of Example 3 and this is attributed to the presence of HPMC. The commercial product, Taxol® (BMS), shows a Cmax only around 26 ng/ml (Group B in FIG. 2) when it is dosed orally, and this is approximately 10-fold lower than that obtained with the compositions of the present invention.

DETAILED DESCRIPTION OF THE INVENTION

Figure 1:
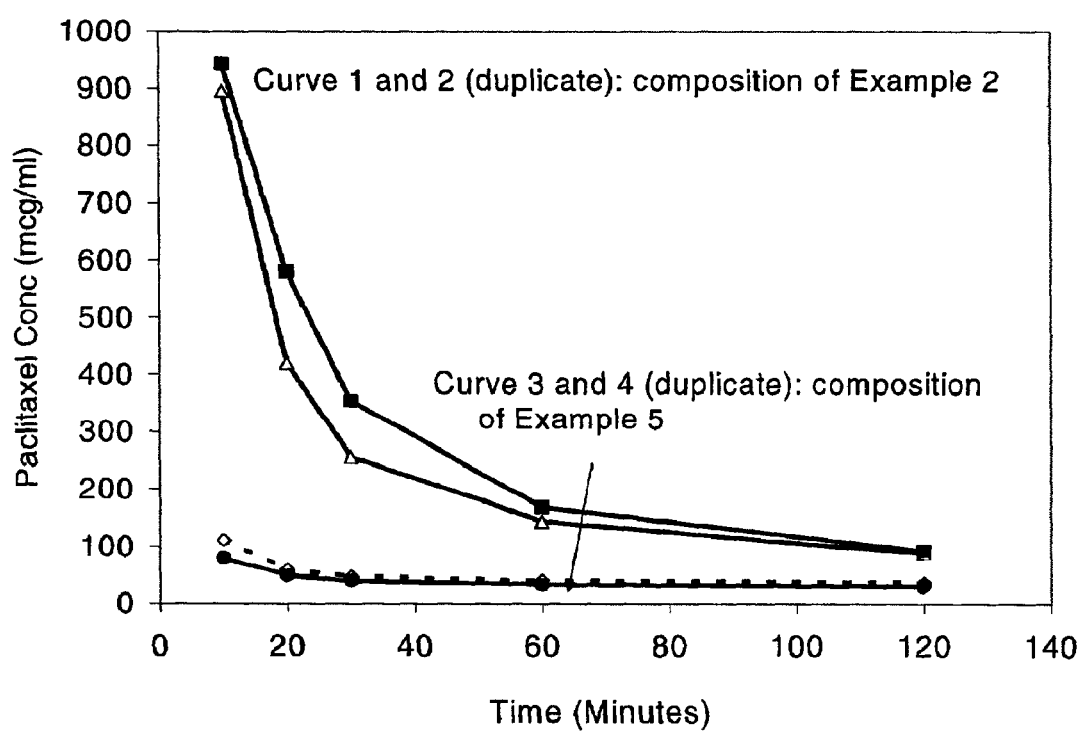
FIG. 1 is a graph depicting paclitaxel concentrations in simulated gastric fluid (SGF, 0.01 N HCl, pH 2) from 60 mg/g paclitaxel compositions with and without HPMC during dissolution of the composition (dilution factor=50×), in which curves 1 and 2 depict paclitaxel concentrations from the composition of Example 2 that contains 4.76% HPMC and curves 3 and 4 depict paclitaxel concentrations from the composition of Example 5 that is substantially similar to Example 2 except that it contained no HPMC. The addition of HPMC in the formulation leads to surprisingly higher paclitaxel concentrations in the SGF medium, generating a supersaturated paclitaxel solution.

Novel pharmaceutical compositions according to the present invention comprise:
- a) paclitaxel or an analog thereof,
- b) a pharmaceutically acceptable solvent,
- c) a pharmaceutically acceptable surfactant, and
- d) a substituted cellulosic polymer.

The compositions of the present invention are self-emulsifying liquid formulations. The term "self-emulsifying liquid formulations" used herein refers to concentrated liquid compositions capable of generating emulsions or microemulsions upon mixing with sufficient aqueous media such as water, infusion fluids, simulated gastric fluid, or actual gastrointestinal fluid. The term "simulated gastric fluid" used herein refers to an aqueous solution of about 0.01 M hydrochloric acid with about 0.15 M sodium chloride, having a pH of about 2. The size of the emulsion or microemulsion droplets generated by the compositions of the present invention are generally below 500 nm and preferably below 150 nm.

The paclitaxel compositions of the present invention can contain paclitaxel generally in an amount up to about 100 mg/gm, preferably from about 10 to about 80 mg/gm, more preferably from about 30 to 70 mg/gm, and even more preferably from about 40 mg/gm to about 65 mg/gm.

The pharmaceutically acceptable solvents suitable for the present invention include polyethylene glycol (PEG series such as PEG 300, 400, 600, etc), propylene glycol, ethanol, glycerol, triacetin, glycofurol, propylene carbonate, dimethyl acetamide, dimethyl isosorbide, N-methyl pyrrolidinone, or a mixture thereof. The preferred solvents of the present invention include polyethylene glycol (PEG series), propylene glycol, ethanol, or a mixture thereof. The total amount of the solvent present in the composition is generally from about 100 to about 700 mg/g and preferably from about 250 to about 400 mg/g.

The pharmaceutically acceptable surfactants suitable for the present invention are non-ionic surfactants including polyoxyl 40 hydrogenated castor oil (sold under the trade name Cremophor RH40®), polyoxyl 35 castor oil (sold under the trade name Cremophor EL®), polyoxyethylene sorbitan fatty acid esters (polysorbates), poloxamers (Pluronics), vitamin E-TPGS 1000 (VE-TPGS 1000), polyoxyethylene alkyl ethers, Solutol HS-15, Tagat TO, Peglicol 6-oleate, polyoxyethylene sterates, or saturated polyglycolyzed glycerides, all of which are commercially available. The preferred surfactants include polyoxyl 40 hydrogenated castor oil (Cremophor RH40®), polyoxyl 35 hydrogenated castor oil (Cremophor EL®), polyoxyethylene sorbitan fatty acid esters (polysorbates), poloxamers (Pluronics), and vitamin E-TPGS 1000. The total amount of the surfactant present in the composition is generally from about 100 to about 700 mg/g, and preferably from about 300 to about 500 mg/g.

The weight ratio of paclitaxel to the surfactant, such as polyethoxylated castor oil, in the compositions of the present invention is preferably between 1:3 to 1:20, and more preferably between 1:5 to 1:10 by weight. The content of polyethoxylated castor oil relative to the content of paclitaxel in the composition is considerably lower in the compositions of the present invention than that in the Taxol® formulation.

The term "substituted cellulosic polymer" used herein refers to a cellulosic polymer having at least a portion of substitutable hydroxyl groups substituted with methoxyl and/or hydroxypropyl groups. We have discovered that such cellulosic polymers can substantially inhibit the precipitation and/or crystallization of paclitaxel or analogs thereof when the composition is exposed to an aqueous medium, such as simulated gastric fluid (SGF). The substituted cellulosic polymer as defined above functions, and is sometimes referred to herein, as a "crystallization inhibitor." Accordingly, the compositions of the present invention comprise at least one substituted cellulosic polymer. Preferably, the substituted cellulosic polymer is substantially water-soluble. Examples of the preferred substituted cellulosic polymers suitable in the present invention include hydroxypropyl methylcellulose (HPMC), hydroxypropyl cellulose (HPC), methylcellulose, hydroxyethylcellulose, maltodextrin, and povidones. More preferably, the substituted cellulosic polymer is HPMC, HPC, hydroxyethylcellulose, methylcellulose, and povidones. Even more preferably, the substituted cellulosic polymer is HPMC.

Suitable HPMCs that are relatively hydrophilic in nature are illustratively available under the brand names Methocel™ (Dow Chemical Co.) and Metolose™ (Shin-Etsu Chemical Co.).

HPMC, useful in the present invention preferably has a viscosity of about 1 to about 100,000 cps when the concentration is about 2% (w/w) in water. The low viscosity HPMC polymer is preferred. HPMC polymers that show a viscosity of 3 to 500 cps in water with 2% concentration is most preferred.

HPMC polymers vary in the degree of substitution of available hydroxyl groups on the cellulosic backbone by methoxyl groups and by hydroxypropyl groups. With increasing hydroxypropyl substitution, the resulting HPMC becomes more hydrophilic in nature. The HPMC polymer preferably have about 15% to about 35%, more preferably about 19% to about 30%, and most preferably about 19% to about 24%, methoxyl substitution, and having about 3% to about 15%, more preferably about 4% to about 12%, and most preferably about 7% to about 12%, hydroxypropyl substitution.

Examples of the more preferred HPMC include HPMC types 2208 and 2910 which have a normal viscosity of about 1 to 100,000 cps when the polymer concentration is 2% in water. An especially preferred HPMC type is 2910 denoting about 28% to 30% methoxyl substitution and about 7% to about 12% hydroxypropyl substitution, and with a nominal viscosity of about 2 to 4000 cps when the HPMC concentration is 2% in water (w/w).

The cellulosic polymer can be suspended or dissolved in the liquid formulation of the invention, or alternatively, the substituted cellulosic polymer may be present as a component of the wall of the capsule wherein a liquid formulation of the invention is encapsulated. In one embodiment, substantially no HPMC or other substituted cellulosic polymer is present in the liquid but the capsule wall comprises HPMC. The capsule wall preferably comprises predominantly of HPMC.

The substituted cellulosic polymer is present in an amount sufficient to substantially either retard or inhibit drug precipitation and/or crystallization upon dilution of the composition in an aqueous medium. An amount sufficient to "substantially inhibit drug precipitation and/or crystallization" herein means an amount sufficient to prevent, slow, inhibit or delay precipitation of drug from solution and/or to prevent, or inhibit or retard, or delay formation of crystalline drug particles from dissolved drug. The specific amount required of the substituted cellulosic polymer type depends on factors such as the particular polymer type being used and the paclitaxel concentration in the composition. For practical purposes, the amount of the substituted cellulosic polymer needed to inhibit drug crystallization and/or precipitation can be determined according to Test I described below, which can also be used to determine whether a particular polymer type or a mixture of polymers is useful as a crystallization inhibitor in a particular composition of the invention.

TEST I:
  A. A volume of a test composition, either in unencapsulated or encapsulated form, having a polymer component is placed in a volume of simulated gastric fluid (SGF) to form a mixture having a fixed ratio of about 1 g to about 2 g of the composition per 100 ml of SGF.
  B. The mixture is maintained at a constant temperature of about 37° C. and is stirred using type II paddles (USP 24) at a rate of 75 rpm for a period of 4 hours.
  C. At one or more time-points after at least about 15 minutes of stirring but before about 4 hours of stirring, an aliquot of the mixture is drawn and filtered, for example through a non-sterile Acrodisc™ syringe filter with a 0.8 μm Versapor™ membrane.
  D. The filtrate is collected in a vessel.
  E. The drug concentration in the filtrate is measured using high performance liquid chromatography (HPLC).
  F. The test is repeated identically with a comparative formulation that is substantially similar to the test formulation except that it lacks the polymer component. Where the polymer component in the test formulation is present as a component in the solvent liquid, it is replaced in the comparative formulation by polyethylene glycol. Where the polymer component in the test formulation is present as a component of a capsule wall, it is replaced in the comparative formulation with gelatin.
  G. If the drug concentration in the filtrate resulting from the test formulation is greater than that in the filtrate resulting from the comparative formulation without polymer, the polymer component present in the test formulation is deemed to substantially inhibit precipitation and/or crystallization of the drug in simulated gastric fluid.

A crystallization inhibitor such as HPMC, when present in the formulation, is generally present in a total amount of about 1% to about 20%, preferably about 1% to about 15%, and most preferably about 1% to about 10%, by weight of the formulation. Typically, the higher the drug concentration in the composition, the more of the cellulosic polymer will be required to provide a crystallization-inhibiting effect. In general, the cellulosic polymer and drug are present in a ratio of about 50:1 to about 0.1:1, preferably about 10:1 to about 0.1:1 and more preferably about 5:1 to about 0.5:1, by weight.

The use of HPMC as a crystallization inhibitor as provided herein advantageously and substantially improves the bioavailability of paclitaxel and permits a reduction in the amount of the surfactant which is known to cause undesirable side effects when administered orally in large amounts.

A typical composition of the present invention comprises:
  a) paclitaxel or an analog thereof at an amount of up to 100 mg/g;
  b) a pharmaceutically acceptable solvent in an amount of from about 100 to about 700 mg/g;
  c) a pharmaceutically acceptable surfactant in an amount of from about 100 to about 700 mg/g; and
  d) a substituted cellulosic polymer in an amount of from about 10 to about 300 mg/g.

In a preferred embodiment, the composition of the present invention comprises:
  a) paclitaxel or an analog thereof at an amount of up to 100 mg/g;
  b) a pharmaceutically acceptable solvent selected from the group consisting of polyethylene glycol (PEG series), propylene glycol, ethanol, or a mixture thereof.
  c) a pharmaceutically acceptable surfactant selected from the group consisting of polyoxyl 40 hydrogenated castor oil, polyoxyl 35 castor oil, polyoxyethylene sorbitan fatty acid esters, poloxamers, and Vitamin E-TPGS 1000; and
  d) a substituted cellulosic polymer selected from the group consisting of HPMC, HPC, methylcellulose, hydroxyethylcellulose, and povidones.

The pharmaceutical compositions according to the present invention may further comprise a diglyceride or a mixture of diglyceride and monoglyceride. The diglycerides and monoglycerides suitable in the present invention are those that contain fatty acids of a carbon chain having 8 to 22 carbons with 0 to 3 double bonds. Examples of suitable fatty acids for the diglycerides and monoglycerides include caprylic acid, capric acid, lauric acid, myristic acid, palmitic acid, stearic acid, oleic acid, linoleic acid, linolenic acid, and docosahexaenoic acid. It is preferred that the fatty acids that are contained in the diglycerides and monoglycerides suitable for the present invention have a carbon chain of 16 to 18 carbons with 1–2 double bonds, such as oleic acid and linoleic acid. The preferred diglyceride is diolein, dilinoleate, or a mixture of diolein and dilinoleate. The most preferred diglyceride is diolein. The preferred monoglyceride is monoolein, monolinoleate, or a mixture of monoolein and monolinoleate. The most preferred monoglyceride is monoolein.

All of the glycerides of the present invention are known and can be prepared by conventional methods. The mixture of diglyceride and monoglyceride may be prepared by mixing individual diglyceride and monoglyceride in appropriate relative proportion or by partial hydrolysis of triglyceride, or by transesterification reaction of triglycerides, or diglycerides with glycerol.

If employed, the diglyceride in the absence of monoglyceride in the composition, or the mixture of the diglyceride and monoglyceride present in the composition is generally from about 10% to about 90%, preferably from about 40% to about 70%, and more preferably from about 50% to about 60%, by weight relative to the total weight of the composition. When a mixture of diglyceride and mono-glyceride is used in the composition, the ratio of diglyceride is to monoglyceride (diglyceride:monoglyceride) by weight is preferably from about 9:1 to about 6:4.

The compositions of the present invention for use by oral administration may further comprise a P-glycoprotein inhibitor. Through the use of P-glycoprotein inhibitors, the paclitaxel more readily transverses the mucosal cells of the small intestine and is therefore more readily absorbed into the systemic circulation.

Thus, in a preferred embodiment, the compositions of the present invention comprises:
  a) paclitaxel or an analog thereof;
  b) a pharmaceutically acceptable surfactant;
  c) a pharmaceutically acceptable solvent;
  d) a substituted cellulosic polymer; and
  e) a P-glycoprotein inhibitor.

In another preferred embodiment, the composition containing a P-glycoprotein inhibitor as defined above further comprises a diglyceride or a mixture of diglyceride and monoglyceride.

The P-glycoprotein inhibitors useful in the compositions of the present invention are those that are described in U.S. Pat. Nos. 5,968,972 and 6,028,054. The compounds that may be used as p-glycoprotein inhibitors and the amounts of such compounds that are required to sufficiently inhibit p-glycoprotein can be identified by the method and process described in U.S. Pat. No. 6,028,054. The full disclosure of U.S. Pat. Nos 5,968,972 and 6,028,054 is incorporated herein by reference. Examples of the preferred P-glycoprotein inhibitors useful in the compositions of the present invention include alginates, xanthan, gellan gum, CRK-1605, cyclosporin A, verapamil, tamoxifen, quinidine, valspodar, SDZ PSC 833, GF120918 (GG918, GW0918), ketocomazole, Psoralens, sucroster-15, R101933, OC144-093, Erythromycin, azithromycin, RS-33295-198, MS-209, XR9576, phenothiazine. The P-glycoprotein inhibitor is incorporated in the paclitaxel compositions of the present invention in an amount of from about 0.1 to about 20 mg/kg body weight. The specific amount of the P-glycoprotein inhibitor required in the composition depends on factors such as the particular P-glycoprotein inhibitor used and the weight of the patients being treated.

The compositions of the present invention may be prepared in a conventional manner, for example, by dissolving paclitaxel in the solvent, then adding the surfactant, the substituted cellulosic polymer, and optionally the diglyceride or the mixture of diglyceride and monoglyceride. The resulting solution can then be formulated into the desired dosage form such as, for example, soft elastic gelatin capsules or hard gelatin capsules by known manufacturing technology. In an alternate embodiment, the cellulosic polymer is not suspended in fill solution, but, instead, the cellulosic polymer is in the capsule shell as in an HPMC capsule.

The compositions of the present invention can be prepared in any one of a number of alternate delivery systems known in the art. For example, the composition may be filled into a soft or hard gelatin capsule, or other oral dosage forms. Any suitable encapsulation material, for example, gelatin or HPMC, can be used. As indicated hereinabove, HPMC can be an advantageous material for use in the capsule wall because it can act as a precipitation and/or crystallization inhibitor upon exposure of the composition to the gastrointestinal fluid. A substituted cellulosic polymer component such as HPMC is "present in the capsule wall" or is a "capsule wall component" as described herein if the polymer is (a) dispersed or mixed together with any other capsule wall component(s), (b) the only capsule wall component, or (c) present as a coating on the outside or inside of the capsule wall.

In a presently preferred embodiment, a substituted cellulosic polymer as described hereinabove, preferably HPMC, is present in the capsule wall in a total amount of about 5% to 100%, and preferably about 15% to most preferably to 100%, by weight of the wall. In addition to one or more such cellulosic polymers, the suitable capsule wall can comprise any additional component useful in the art such as gelatin, starch, carrageenan, sodium alginate, plasticizers, potassium chloride, coloring agents, etc.

Where a crystallization-inhibiting cellulosic polymer is present as the capsule wall or as a component of the capsule wall, the solution or solution/suspension contained therein can additionally, but optionally, comprise a further amount of the same polymer or a different substituted cellulosic polymer.

Concentrated solutions or solutions/suspensions can be encapsulated by any method known in the art including the plate process, vacuum process, or the rotary die process. See, for example, Ansel et al. (1995) in *Pharmaceutical Dosage Forms and Drug Delivery Systems,* 6th ed., Williams & Wilkins, Baltimore, Md., pp. 176–182. By the rotary die process, liquid encapsulation material, for example gelatin, flowing from an overhead tank is formed into two continuous ribbons by a rotary die machine and brought together by twin rotating dies. Simultaneously, metered fill material is injected between ribbons at the same moment and the dies form pockets within the ribbons. These pockets of fill-containing encapsulation material are then sealed by pressure and heat, and the capsules are dispersed from the machine.

Soft gelatin capsules can be manufactured in different shapes including round, oval, oblong, and tube-shape, among others. Additionally, by using two different ribbon colors, two-tone capsules can be produced.

Capsules that comprise HPMC are known in the art and can be prepared, sealed and/or coated, by way of non-limiting illustration, according to processes disclosed in the patents and publications listed below, each of which is individually incorporated herein by reference.

U.S. Pat. No. 4,250,997 to Bodenmann et al.
U.S. Pat. No. 5,264,223 to Yamamoto et al.
U.S. Pat. No. 5,756,123 to Yamamoto et al.
International Patent Publication No. WO 96/05812.
International Patent Publication No. WO 97/35537.
International Patent Publication No. WO 00/18377.
International Patent Publication No. WO 00/27367.
International Patent Publication No. WO 00/28976.
International Patent Publication No. WO 01/03676.
European Patent Application No. 0 211 079.
European Patent Application No. 0 919 228.
European Patent Application No. 1 029 539.

Non-limiting illustrative examples of suitable HPMC-comprising capsules include capsules manufactured and distributed by BioProgress (XGel™), Capsugel, and Shionogi Qualicaps™.

In another embodiment, compositions of the invention are provided that are required to be diluted to provide a dilution suitable for direct, imbibable administration. In this embodiment, the compositions of the present invention are added, in a therapeutically effective dosage amount, to about 1 ml to about 20 ml of an inert liquid. Preferably compositions of the present invention are added to about 2 ml to about 15 ml, and more preferably to about 5 ml to about 10 ml, of inert liquid. The term "inert liquid" as used herein refers to pharmaceutically acceptable, preferably palatable liquid carriers. Such carriers are typically aqueous. Examples include water, fruit juices, carbonated beverages, etc.

EXAMPLES

Example 1 below is an example of the procedures that can be used to prepare the compositions of the present invention. Examples 2–4 are provided to more specifically detail particular embodiments of the novel compositions of the present invention. Examples 1–4 are provided for illustrative purposes only however, and it is recognized that minor changes and alterations can be made with respect to the particular ingredients and their disclosed amounts, or with respect a particular step of the procedure for preparing the composition. It is to be understood that to the extent any such changes do not in fact materially alter and/or re-formulate the final composition, such changes are to be considered as falling within the spirit and scope of the invention as recited by the claims that follow.

The compositions of Examples 5 and 6 below are provided for comparative purposes only. The composition of Example 5 is substantially similar to the composition of Example 2 except that it contains no substituted cellulosic polymer (HPMC). A comparative dissolution testing comparing the composition of Example 5 with that of Example 2, was conducted and the result of which is graphically depicted in FIG. 1.

Figure 2:
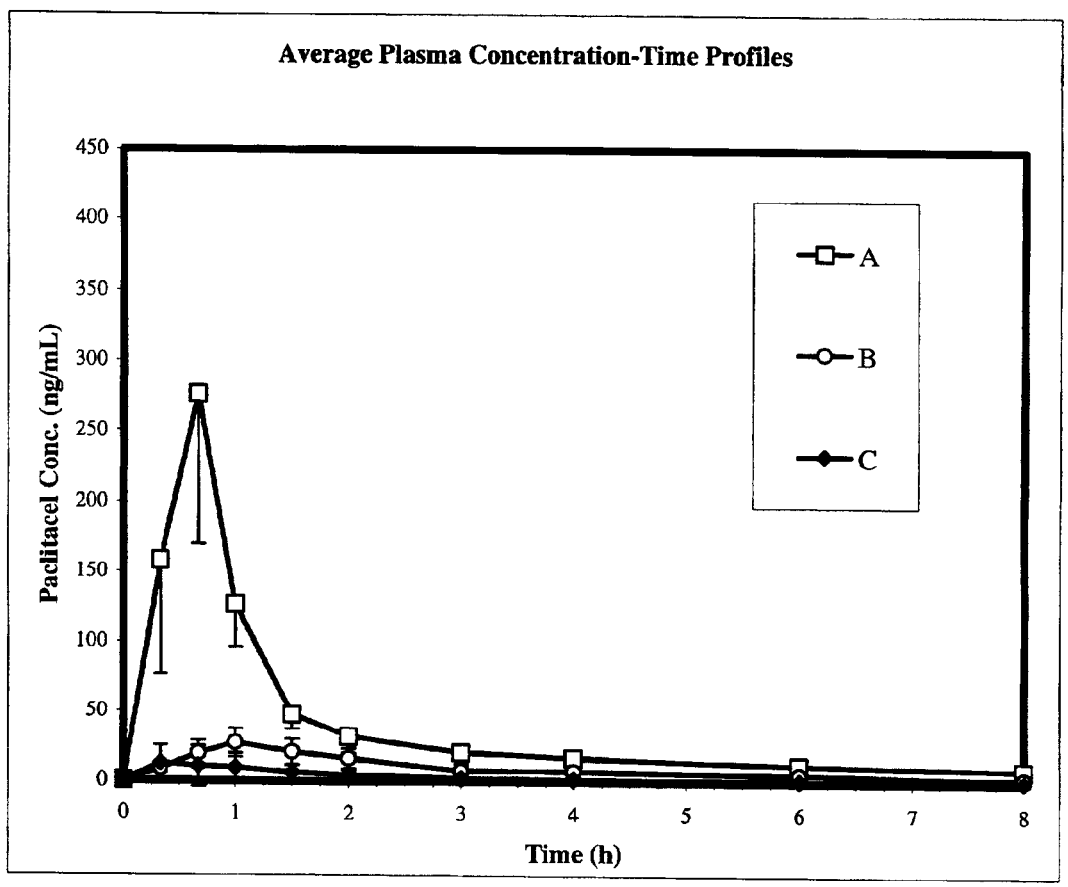
FIG. 2 is a graph depicting the levels of paclitaxel in plasma samples taken over a period of 8 hours from groups of rats. In one group (A), the composition of Example 3 which contains HPMC was administered orally. In a second group (B), the commercial formulation Taxol® was administered orally. In a third group (C), a paclitaxel composition (Example 6) substantially similar to that of Example 3 with the major exception that it contained no HPMC was administered orally. The total dose of paclitaxel administered to each rat in each group was 10 mg/kg.

The compositions of Examples 6 is substantially similar to the composition of Example 3 except that it contains no substituted cellulosic polymer (HPMC). A comparative pharmacokinetics study was conducted in which the pharmacokinetics of the compositions of Example 6 and Taxol were compared with the composition of Example 3, another preferred composition of the present invention, and the result of which is graphically depicted in FIG. 2.

Example 1
Procedure for Preparing the Compositions of the Present Invention

Drug is placed in a vial and the appropriate amount of solvent or a mixture of solvents (such as PEG 400 and ethanol with an appropriate ratio) is added into the vial. The vial is then capped. The vial is put into a water bath of about 50–60° C. and shaken gently until all of the drug material is completely dissolved. After the vial is cooled to room temperature, an appropriate amount of surfactant (such as Cremophor EL) is added and followed by the mixture of mono- and di-glycerides of fatty acids, if any. The vial is then capped and placed into the water bath of about 50–60° C. The vial is shaken gently to obtain a clear, uniform solution. This solution can be filled into HPMC capsules and stored at room temperature before oral dosing. Alternatively, the substituted polymer powders (such as HPMC) can be added into the solution with adequate agitation (i.e., stirring, shaking) to obtain a uniform polymer suspension. The resulting composition can then be filled into either soft gelatin or hard gelatin capsules and stored at room temperature before oral dosing.

Example 2

| Component | Amount (mg/g) |
|---|---|
| Paclitaxel | 57.2 |
| Absolute ethanol | 152.1 |
| PEG-400 | 152.1 |
| Cremophor EL | 400 |
| Glyceryl dioleate | 190 |
| HPMC-E5 | 47.6 |
| Total | 1000 |

Example 3

| Component | Amount (mg/g) |
|---|---|
| Paclitaxel | 57 |
| Absolute ethanol | 151.5 |
| PEG-400 | 151.5 |
| Cremophor EL | 400 |
| Glyceryl dioleate | 190 |
| HPMC-E5 | 50 |
| Total | 1000 |

Example 4

| Component | Amount (mg/g) |
|---|---|
| Paclitaxel | 60 |
| Absolute ethanol | 150 |
| PEG-400 | 150 |
| Cremophor EL | 400 |
| Glyceryl dioleate | 160 |
| HPMC-E5 | 50 |
| Cyclosporin A | 30 |
| Total | 1000 |

Example 5

| Component | Weight (mg/g) |
|---|---|
| Paclitaxel | 65 |
| Absolute ethanol | 160 |
| PEG-400 | 160 |
| Cremophor EL | 415 |
| Glyceryl dioleate | 200 |
| Total | 1000 |

Example 6

| Component | Amount (mg/g) |
|---|---|
| Paclitaxel | 62.5 |
| Absolute ethanol | 156.25 |
| PEG-400 | 156.25 |
| Cremophor EL | 417 |
| Glyceryl dioleate | 208 |
| Total | 1000 |

What is claimed is:

1. A composition for administering paclitaxel, wherein:
   the composition is self-emulsifying;
   the composition comprises:
      (a) a paclitaxel or an analog thereof;
      (b) a pharmaceutically acceptable surfactant;
      (c) a pharmaceutically acceptable solvent; and
      (d) a substituted cellulosic polymer;
   the paclitaxel and surfactant are present in a ratio of from about 1:3 to about 1:20 by weight; and
   the substituted cellulosic polymer and paclitaxel are present in a ratio of from about 50:1 to about 0.1:1 by weight.

2. The composition of claim 1 which is for oral administration.

3. The composition of claim 1 wherein said surfactant is selected from the group consisting of polyoxyl 40 hydrogenated castor oil, polyoxyl 35 hydrogenated castor oil, polyoxyethylene sorbitan fatty acid esters, poloxamers, VE-TPGS 1000, polyoxyethylene alkyl ethers, Solutol HS-15, Tagat TO, Peglicol 6-oleate, polyoxyethylene sterates, and saturated polyglycolyzed glycerides.

4. The composition of claim 3 wherein said surfactant is selected from the group consisting of polyoxyl 40 hydrogenated castor oil, polyoxyl 35 hydrogenated castor oil, polyoxyl sorbitan fatty acid esters, poloxamers, and VE-TPGS 1000.

5. The composition of claim 4 wherein said surfactant is a polyoxyl 40 hydrogenated castor oil or polyoxyl 35 hydrogenated castor oil.

6. The composition of claim 1 wherein the weight ratio of paclitaxel to the surfactant (paclitaxel:surfactant) is from about 1:5 to about 1:10.

7. The composition of claim 1 wherein said solvent is selected from the group consisting of polyethylene glycol, propylene glycol, ethanol, glycerol, triacetin, glycofurol, propylene carbonate, dimethyl acetamide; dimethyl isosorbide, N-methyl pyrrolidinone, and a mixture thereof.

8. The composition of claim 7 wherein said solvent is selected from the group consisting of polyethylene glycol, propylene glycol, ethanol, and a mixture thereof.

9. The composition of claim 8 wherein said solvent is a mixture of ethanol and a polyethylene glycol consisting of polyethylene glycol 400.

10. The composition of claim 1 wherein the said substituted cellulosic polymer is selected from the group consisting of hydroxypropyl methylcellulose (HPMC), hydroxypropyl cellulose (HPC), hydroxyethylcellulose, methylcellulose, maltodextrin, and povidones.

11. The composition of claim 10 wherein the said substituted cellulosic polymer is selected from the group consisting hydroxypropyl methylcellulose, hydroxyethylcellulose, hydroxypropyl cellulose, and methylcellulose.

12. The composition of claim 11 wherein said substituted cellulosic polymer is hydroxypropyl methylcellulose.

13. The composition of claim 1 wherein said substituted cellulosic polymer and paclitaxel are present in a ratio of about 10:1 to about 0.1:1 by weight.

14. The composition of claim 13 wherein said substituted cellulosic polymer and paclitaxel are present in a ratio of about 5:1 to about 0.5:1 weight.

15. The composition of claim 1 wherein said substituted cellulosic polymer is substantially water-soluble.

16. The composition of claim 12 wherein the hydroxypropyl methylcellulose has about 15% to about 35% methoxyl substitution and about 4% to about 15% hydroxypropyl substitution.

17. The composition of claim 16 wherein the hydroxypropyl methylcellulose has about 19% to about 24% methoxyl substitution and about 7% to about 12% hydroxypropyl substitution.

18. The composition of claim 2 which is contained in a water-soluble capsule.

19. The composition of claim 18 wherein the substituted cellulosic polymer is present in the capsule wall.

20. The composition of claim 19 wherein the substituted cellulosic polymer constitutes from about 5% to 100% by weight of the capsule wall.

21. The composition of claim 20 wherein the substituted cellulosic polymer constitutes from about 5% to 100% by weight of the capsule wall.

22. The composition of claim 1 which further comprises a diglyceride.

23. The composition of claim 22 wherein the diglyceride contains fatty acids of a carbon chain having 8 to 22 carbons with 0 to 3 double bonds.

24. The composition of claim 23 wherein the diglyceride contains fatty acids of a carbon chain having 16 to 18 carbons with 1–2 double bonds.

25. The composition of claim 22 wherein the diglyceride is selected from the group consisting of diolein, dilinoleate, and a mixture thereof.

26. The composition of claim 22 which further comprises a monoglyceride.

27. The composition of claim 26 wherein the monoglyceride contains fatty acids of a carbon chain having 8 to 22 carbons with 0 to 3 double bonds.

28. The composition of claim 26 wherein the monoglycerides contains fatty acids of a carbon chain having 16 to 18 carbons with 1–2 double bonds.

29. The composition of claim 26 wherein the monoglyceride is selected from the group consisting of monoolein, monolinoleate, and a mixture thereof.

30. The composition of claim 26 wherein the ratio of diglyceride to monoglyceride (diglyceride:monoglyceride) by weight is from about 9:1 to about 6:4.

31. The composition of claim 1 wherein the paclitaxel is present in an amount of up to about 100 mg/gm.

32. The composition of claim 31 wherein the paclitaxel is present in an amount of from about 10 to about 80 mg/gm.

33. The composition of claim 32 wherein the paclitaxel is present in an amount of from about 30 to 70 mg/gm.

34. The composition of claim 33 wherein the paclitaxel is present in an amount of from about 40 mg/gm to about 65 mg/gm.

35. The composition of claim 1 wherein said surfactant is present in an amount from about 100 to about 700 mg/g.

36. The composition of claim 1 wherein said solvent is present in an amount from about 100 to about 700 mg/g.

37. The composition of claim 2 further comprising a P-glycoprotein inhibitor.

38. The composition of claim 37 wherein said P-glycoprotein inhibitor is selected from the group consisting of alginates, xanthan, gellan gum, CRK-1605, cyclosporin A, verapamil, tamoxifen, quinidine, valspodar, SDZ PSC 833, GF120918 (GG918, GW0918), ketocomazole, Psoralens, sucroster-15, R101933, OC144-093, Erythromycin, azithromycin, RS-33295-198, MS-209, XR9576, and phenothiazine.

39. The composition of claim 38 wherein said P-glycoprotein inhibitor is cyclosporin A.

40. The composition of claim 39 wherein said cyclosporin A in the composition is in an amount of from about 0.1 to about 20 mg/kg patient body weight.

41. The composition of claim 1 wherein the surfactant is selected from the group consisting of polyoxyl 40 hydrogenated castor oil, polyoxyl 35 hydrogenated castor oil, polyoxyethylene sorbitan fatty acid esters, poloxamers, vitamin E-TPGS 1000, polyoxyethylene alkyl ethers, Solutol HS-15, Tagat TO, Peglicol 6-oleate, polyoxyethylene sterates, and saturated polyglycolyzed glycerides; and wherein the substituted cellulosic polymer is selected from the group consisting of hydroxypropyl methylcellulose (HPMC), hydroxypropyl cellulose (HPC), hydroxyethylcellulose, methylcellulose, maltodextrin, and povidones.

42. The composition of claim 41 wherein the surfactant is selected from the group consisting of a polyoxyl 40 hydrogenated castor oil and a polyoxyl 35 hydrogenated castor oil; wherein the solvent is selected from the group consisting of polyethylene glycol, propylene glycol, ethanol, and a mixture thereof; and wherein the substituted cellulosic polymer is selected from the group consisting of hydroxypropyl methylcellulose, hydroxypropyl cellulose, hydroxyethylcellulose, and methylcellulose.

43. The composition of claim 42 wherein the surfactant is a polyoxyl 35 hydrogenated castor oil; wherein the solvent is a mixture of polyethylene glycol ethanol; and wherein the substituted cellulosic polymer is hydroxypropyl methylcellulose.

44. The composition of claim 42 further comprising a diglyceride.

45. The composition of claim 44 wherein the diglyceride is glyceryl dioleate.

46. A method of treating a patient suffering from cancer and in need of treatment, wherein:
   the method comprises administering a self-emulsifying composition to the patient;
   the composition comprises:
     a) a chemotherapeutically effective amount of paclitaxel,
     b) a pharmaceutically acceptable surfactant,
     c) a pharmaceutically acceptable solvent, and
     d) a substituted cellulosic polymer;
   the paclitaxel and surfactant are present in a ratio of from about 1:3 to about 1:20 by weight; and
   the substituted cellulosic polymer and paclitaxel are present in a ratio of from about 50:1 to about 0.1:1 by weight.

47. The method of claim 46 wherein the amount of said paclitaxel in the composition is from about 10 to about 80 mg/g.

48. The method of claim 47 wherein the amount of said paclitaxel in the composition is from about 30 to about 70 mg/g.

49. The method of claim 48 wherein the amount of said paclitaxel in the composition is from about 40 to about 65 mg/g.

50. The method of claim 46 wherein said composition further comprises a diglyceride.

51. The method of claim 50 wherein said composition further comprises a monoglyceride.

52. The method of claim 51 wherein the ratio of the diglyceride to monoglyceride, by weight, in the composition is from about 9:1 to about 6:4.

53. The method of claim 50 wherein the composition is administered orally.

54. The method of claim 53 wherein the composition further comprises a P-glycoprotein inhibitor.

55. The method of claim 54 wherein said P-glycoprotein inhibitor is selected from the group consisting of cyclosporin A, verapamil, tamoxifen, quinidine, phenothiazine, and mixtures thereof or related P-glycoprotein inhibitors.

56. The method of claim 54 wherein the amount of said P-glycoprotein inhibitor in the composition is from about 0.1 to about 20 mg/kg patient body weight.

57. The composition of claim 12 wherein the hydroxypropyl methylcellulose has a viscosity range of about 1 to 1 about 100,000 cps.

58. The composition of claim 57 wherein the hydroxypropyl methylcellulose has a viscosity range of about 1 to about 4,000 cps.

59. The composition of claim 12 wherein the hydroxypropyl methylcellulose is type 2208 or 2910.

60. The composition of claim 18 wherein the substituted cellulosic polymer is present in the fill liquid composition of the water-soluble capsule.

61. The composition of claim 1 which generates a supersaturated state upon dilution with water.

* * * * *